United States Patent [19]
Polyak et al.

[11] Patent Number: 5,263,981
[45] Date of Patent: Nov. 23, 1993

[54] IMPLANTABLE PENILE PROSTHESIS

[75] Inventors: Mark Polyak, Minnetonka; Robert W. Pugh, Jr., Lakeville, both of Minn.

[73] Assignee: American Medical Systems, Inc., Minnetonka, Minn.

[21] Appl. No.: 873,473

[22] Filed: Apr. 24, 1992

[51] Int. Cl.$^5$ .............................................. A61F 2/26
[52] U.S. Cl. ............................................ 623/12; 600/40
[58] Field of Search ..................... 128/79, DIG. 25; 623/10, 11, 8

[56] References Cited

U.S. PATENT DOCUMENTS

| | | | |
|---|---|---|---|
| 3,853,122 | 12/1974 | Strauch et al. | 128/79 |
| 3,954,102 | 5/1976 | Buuck | 128/79 |
| 4,009,711 | 3/1977 | Uson | 128/79 |
| 4,267,829 | 5/1981 | Burton et al. | 128/79 |
| 4,353,360 | 10/1982 | Finney et al. | 128/79 |
| 4,360,010 | 11/1982 | Finney | 128/79 |
| 4,369,771 | 1/1983 | Trick | 128/79 |
| 4,399,811 | 8/1983 | Finney et al. | 128/79 |
| 4,590,927 | 5/1986 | Porter et al. | 128/79 |
| 4,596,242 | 6/1986 | Fischell | 128/79 |
| 4,726,360 | 2/1988 | Trick et al. | 128/79 |
| 4,773,403 | 9/1988 | Daly | 128/79 |
| 4,782,826 | 11/1988 | Fogarty | 128/79 |
| 4,791,917 | 12/1988 | Finney | 128/79 |
| 5,010,882 | 4/1991 | Polyak et al. | 128/79 |
| 5,048,510 | 9/1991 | Hauschild et al. | 128/79 |

Primary Examiner—David Isabella
Attorney, Agent, or Firm—Peter C. Richardson; Lawrence C. Akers; Michael J. Pantuliano

[57] ABSTRACT

A penile prosthesis for alleviating erectile impotency includes a generally tubular enclosure which is implantable within the corpus cavernosum. The tubular enclosure includes a generally non-distensible pressurizable chamber which when filled with fluid substantially to capacity will transform the prosthesis from the flaccid to an erect state, and a unique inflation valve assembly comprising two valves in longitudinally sequential relationship which will open or close under sequentially applied pressure differential conditions. The prosthesis includes a pump implantable in the body apart from the tubular enclosure, preferably in the scrotum, and a deflation valve.

13 Claims, 6 Drawing Sheets

IMPLANTABLE PENILE PROSTHESIS

BACKGROUND OF THE INVENTION

This invention relates generally to the field of implantable prosthetic systems for overcoming male erectile impotence, to a method therefore, and more specifically to a penile prosthesis having a unique inflation valve assembly and concomitant improved means for inflating and deflating said prosthesis.

A number of devices are available for enabling those with erectile impotency to achieve an erection. These devices are generally implanted within the corpus cavernosum of the penis. Normally two such devices are utilized, one implanted into each corpus cavernosum. Generally speaking, the penile prostheses which are available, or which have been described, include a reservoir, a pump and a pressure chamber. Fluid is pumped from the reservoir by the pump to the pressure chamber to achieve an erection. Illustrative of the early devices are those disclosed in U.S. Pat. No. 3,853,122 to Strauch, et al., which discloses an external pump and a single tube and valve mechanism, and U.S. Pat. No. 3,954,102 to Buuck, et al. which discloses a device manually operated through the use of bypass valve means.

Further illustrative of the devices available is that disclosed in U.S. Pat. No. 4,590,927 to Porter and Kuyaya. This patent relates to a unitary penile prosthesis which comprises a tubular enclosure having a distal portion which includes a pump, a medial portion including a pressurizable chamber which contains an internal tubular, substantially non-distensible portion and a concentric tubular sleeve, and a proximal portion defining a fluid reservoir therewithin. The non-distensible portion of the pressurizable chamber is typically crimped so that it may expand in diameter. The tubular sleeve may elastically bias the non-distensible portion to its flaccid state. A passageway fluidically connects the reservoir and the pump and is in fluid isolation from the pressurizable chamber of the medial portion.

In U.S. Pat. No. 5,010,882 to Polyak and Pugh there is described an implantable penile prosthesis employing a unique deflation valve mechanism which provides an improved means for returning the prosthesis from the erect to the flaccid state. In its preferred embodiment, the prosthesis of the patent is of a unitary type in which the pump bulb, reservoir, pressurizable chamber, and inflation and deflation valves are in a self-contained unit which is inserted into the corpus cavernosum.

While unitary penile prosthetic devices have distinct advantages, and have achieved substantial success and acceptability, some users have still experienced difficulty in inflating these devices particularly since inflation often requires the squeezing of the tip or other part of the penis, which can be awkward. Therefore, a device which would enable the user to quickly and effectively achieve the inflation of the prosthesis, without sacrificing the sure, facile and quick means for deflating the prosthesis inherent in the unitary type of prosthetic device such as described in U.S. Pat. No. 5,010,882, by, for example, simply squeezing the scrotum, would be very desirable.

SUMMARY OF THE INVENTION

The present invention relates to penile prosthetic devices which are implantable within at least one corpus cavernosum of the penis, said devices including an implantable broadly, i.e. generally, tubular enclosure having a generally tubular pressurizable chamber section defined therewithin which is expandable from a flaccid to an erect state. The devices of this invention are further characterized by an inflation valve assembly defined within the tubular enclosure, comprising two valves in longitudinally sequential relationship, said valves of said assembly having means for opening and closing under sequentially applied pressure differential conditions. Each of the valves in the inflation valve assembly (or block) comprises a normally tightly fitting but distensible sleeve or other suitable structure, which in a closed mode will be compressed on a rigid insert (or stiffener) of the valve assembly, but in an open mode will enable fluid to pass around said insert from an adjacent chamber.

The devices of this invention are further characterized by a pump bulb defined in an area of the body of the patient other than in the corpus cavernosum, such as in the scrotum; said bulb being in fluid communication with the aforesaid valve assembly at a point between the two valves of said assembly.

In the preferred penile prosthesis of this invention the pressurizable chamber is defined medially within the implantable tubular enclosure between a front portion or section which is adapted to be disposed inside the distal portion of a patient's penis, and a rearward portion or section adapted to be implanted within the root or proximal end of the penis. In a further preferred embodiment the front or distal portion is elongated and is substantially rigid and contains a deflation valve mechanism such as defined in U.S. Pat. No. 5,010,882, and the rearward portion contains a fluid reservoir disposed to the rear of the aforesaid inflation valve assembly.

The pressurizable chamber section also preferentially includes a substantially non-distensible tubular portion and a tubular sleeve concentric with said tubular portion; said tubular portion being expandable from a flaccid to an erect, stiff state when the interior volume thereof is filled substantially. Channels in the entire tubular sleeve are defined to permit the flow of fluid during deflation from the pressurizable chamber back to the reservoir.

In the practice of this invention the term of art "fluid" denotes "liquid",

DETAILED DESCRIPTION OF THE DRAWINGS

Figure 1:
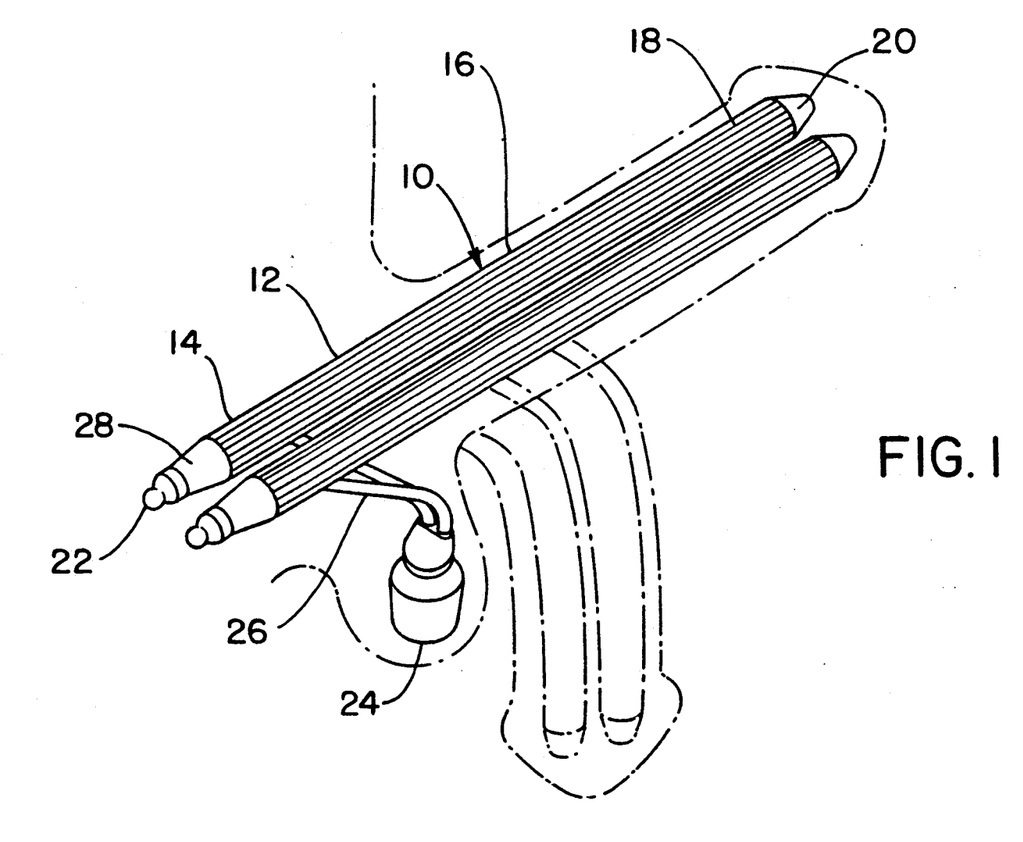
FIG. 1 is a perspective view of a typical prosthesis of the subject invention in its implanted state.

Referring to the drawings, wherein like reference characters are utilized whenever feasible for like parts throughout the several views, a non-unitary inflatable penile prosthetic device 10 is shown in FIG. 1. It comprises an implantable cylinder or tubular enclosure 12, and a pump bulb 24 implantable in the scrotum in fluid communication with cylinder 12. Normally a cylinder 12 is implanted in each corpus cavernosum, both then in fluid communication with the pump bulb 24. However, it is possible to utilize only one cylinder in one corpus cavernosum.

In the prosthesis defined by FIG. 1, the outer layer of the device 10 is composed of a material which is physiologically inert or biocompatible. Illustrative of such material is silicon rubber, but any material known to be useful for artificial devices to be implanted in the body can be employed.

The cylinder 12 depicted in FIG. 1 includes a proximal portion 14, a medial portion 16 and a distal portion 18. In the enlarged cross-sectional view of the device 10 shown in FIG. 2, the proximal portion 14 defines a reservoir 50. Conveniently rear tip 28 has a slightly tapered configuration. A rear tip extender 22, shown in FIG. 1, preferably of the type disclosed in U.S. Pat. No. 5,010,882 may be provided to lengthen the device 10, if desired. Reservoir 50 defines a reservoir chamber 52.

The distal portion 18 shown in FIG. 1 advantageously includes a front tip 20 that is preferably substantially rigid, so as to resist buckling when in use in the erect state. Advantageously the tip 20 is rigid in both the erect and flaccid states. The pump bulb 24 shown in FIG. 1 is typically of the manually compressible type such as for example described in U.S. Pat. No. 4,590,927. Tubing (or tubings) 26, as shown in FIG. 1, enables pump 24 to be in fluid communication with cylinder 12 (or cylinders, if two are used).

Figure 2:
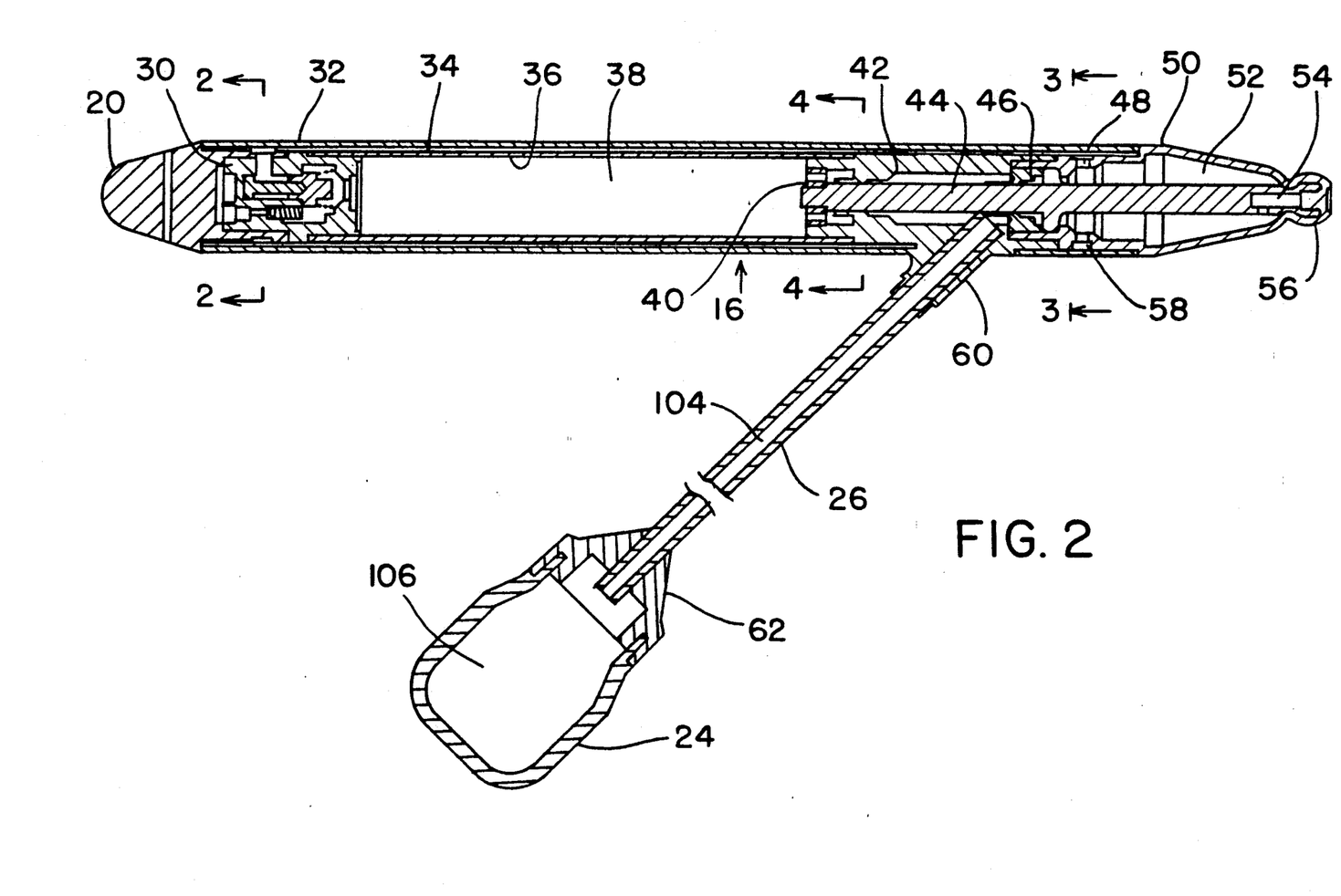
FIG. 2 is a preferred implantable prosthesis in accordance with this invention in a longitudinal cross-sectional view.
Figure 3:
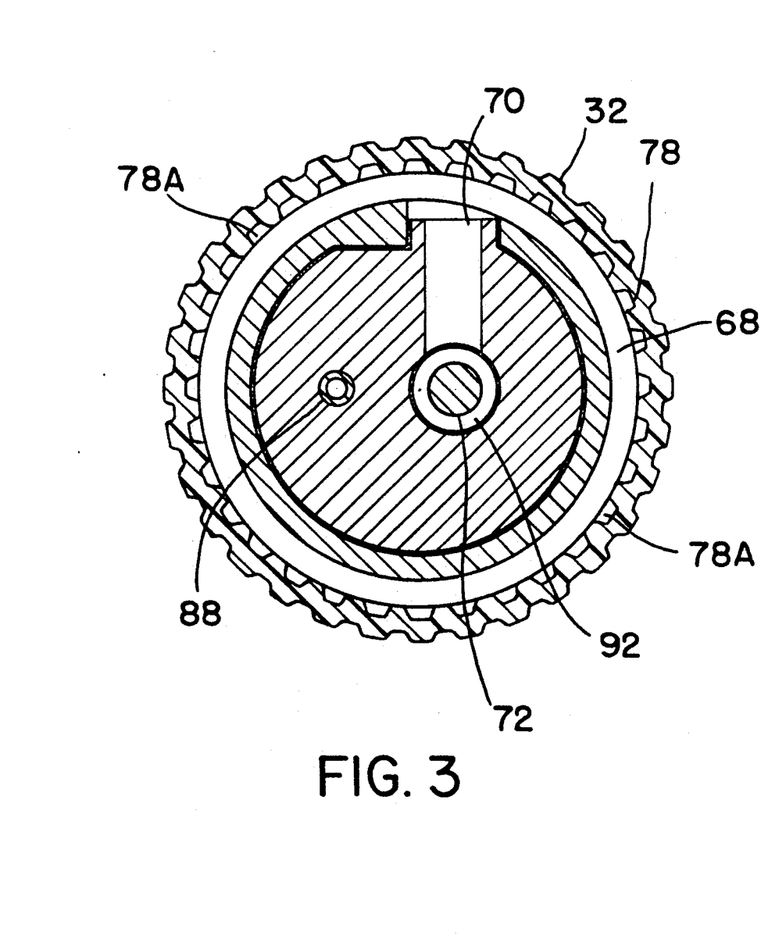
FIG. 3 is a transverse cross-sectional view along the axis 2—2 of the prosthesis of FIG. 2.

As shown in FIG. 2, the medial portion 16 defines a pressurizable chamber 38. This medial portion is positioned along the length of the cylinder 12 so that it is also medially disposed along the length of the corpus cavernosum. Outer layer 32 of said medial portion 16 is preferably comprised of corrugated tubing typically made of a liquid impervious material such as silicone. Concentrically defined within said outer layer 32 is longitudinal passageway 78, shown in FIG. 3. As indicated in FIG. 3, passageway can also be represented as multiple passageways or channels 78A. Pressurizable chamber 38 is defined interiorly of said passageway 78, and is comprised of two layers, i.e. an inner layer (or bladder) 36 and a substantially non-distensible layer 34 which is disposed concentrically about the inner layer 36. The non-distensible layer 34 may be take a variety of forms, but advantageously is formed from a tubular section of woven dacron material, such as a prosthetic vascular graft material. Similarly the inner layer 36 can also take a variety of forms, but advantageously is formed from a tubular section of a liquid impervious material such as silicone. Located in the front end of the cylinder 12 anteriorly to pressurizable chamber 38 is deflation block 30 which will be more definitively described hereinafter with reference to FIG. 4. This block is in fluid communication with reservoir 50 through passageway 78 also as hereinafter described.

In the practice of this invention passageway 78 is, as stated, longitudinally disposed along the length of cylinder 12 between distal portion 18 and proximal portion 14 and serves to convey fluid during deflation, as hereinafter described, back to the reservoir 50.

In the preferred embodiment of this invention, passageway 78 is in reality a series of passageways, as shown more clearly in FIG. 3. These passageways (78A) are interconnected with each other by means of outlet ring channel 68 and reservoir ring channel 58 shown in FIG. 6. The corrugated configuration of outer layer 32 defining the passageways 78A is particularly advantageous in the practice of this invention, because it permits an easier streching of the medial portion when the cylinder 12 is bent or hinged, which as will be shown later is important to the operation of the device. In other words, the corrugated shape serves to assist the assumption of a flaccid mode because there is virtually no resistance to a circumferential re-shaping when the device 10 is hinged in order to assume the flaccid mode. It has also been found that because this configuration re-shapes with a minimum of force, stress upon the silicone of the outer tubing is reduced with improvement in the friction-caused wear-time of said silicone.

As previously considered in U.S. Pat. No. 5,010,882 a vexing problem with most penile implants is their failure to resume the flaccid condition with a minimum of effort and a maximum (or near maximum) of certainty. A unique feature of the invention described in U.S. Pat. No. 5,010,882 was a deflation valve which provides a quick and sure means (and method) for effecting a quick and sure return of the penis containing the penile implant from the erect to flaccid state. In the subject invention, the deflation valve of U.S. Pat. No. 5,010,882 is employed, with slight variations, for the purpose set forth in the aforementioned patent. However, as stated heretofore, in the practice of the subject invention, this valve is usually disposed in the front end of the cylinder 12.

Figure 4:
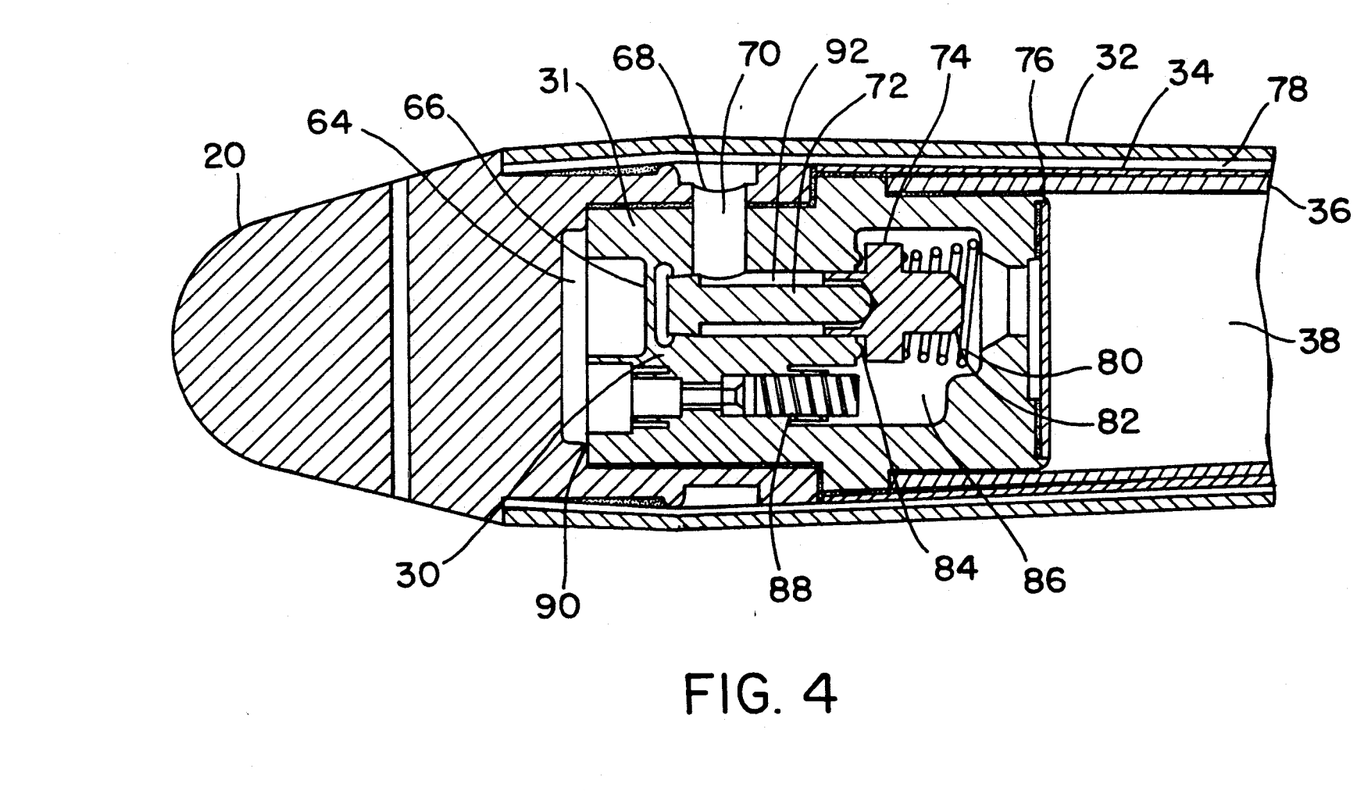
FIG. 4 is an enlarged longitudinal cross-sectional view of the deflation valve shown in FIG. 2.

As shown in FIG. 4, the deflation valve (of valve block 30) operates on a pressure differential basis. In abutting sealing relationship (when the valve is in a closed position which is the normal mode thereof) with housing 31 is a poppet 82 which preferably comprises a head 74 and a shaft 72. Poppet head 74 is typically held in sealing contact with housing 31 by means of precalibrated spring 80 and also by the fluid pressure exerted by the fluid in the rear chamber 86 which is in constant fluid communication with the pressurized chamber 38. When the prosthetic device is either in the flaccid or erect mode, the pressure in front chamber 64 and rear chamber 86 is the same. Front chamber 64 and rear chamber 86 are in fluid communication with each other through fluid resistor means 88. The latter provides a predetermined time-deferred resistance to fluid flow to and from front chamber 64 and rear chamber 86. This element 88 may be of several types known in the art, but typically is one of the kind which defines a labyrinth type fluid passage such as one formed by a plurality of axially aligned, perforated disks which are adapted to define a restrictive path for fluid flow.

An important feature of the valve of block 30 is a movable or distensible partition 66, which is preferably made in the form of a diaphragm; Partition 66 is preferably spaced apart from and in front of poppet shaft 72 and is designed to impact upon the poppet shaft when the pressure in front chamber 64 is sufficiently high. If said pressure is sufficiently higher then the pressure in rear chamber 86, the necessary extent of which is preset and predetermined, the partition 66 will distend and impact upon the poppet shaft with sufficient force to break the sealing contact of the poppet head 74 with valve seat 84 thereby opening the deflation valve. Fluid is allowed to pass from the pressurizable chamber 38 to the reservoir 50 through a fluid communication line formed by middle chamber 92, outlet hole 70, outlet ring channel 68, longitudinal passageways 78(A), reservoir ring channel 58 and inlet hole 48. Middle chamber 92 is, as shown, disposed about the poppet shaft medial to the front chamber 64 and rear chamber 86.

FIG. 3, as shown, depicts a transverse cross-sectional view along the axis 2—2 of FIG. 2 through the deflation valve block 30. This figure shows the relative disposition of the corrugated outer layer 32 and the multiplicity of passageways, represented by 78A. Not shown in this figure is the non-distensible layer 34 referred to with respect to pressurizable chamber 38, which layer extends into and is fixed onto the outer surface of the housing 31 of deflation valve block 30. It also extends to the external surface of the inflation block 42 shown in FIG. 6 and is also affixed thereto.

Returning to FIG. 2, located to the rear of pressurizable chamber 38 is a unique feature of this invention, namely inflation assembly or block 42. The latter will be more definitively described hereinafter with reference to FIG. 6. Inflation block 42 is defined within the aforementioned proximal portion 18. Disposed separately from cylinder 12, such as in the scrotum, is pump bulb 24. If desired, pump bulb 24 can be located elsewhere in the body, e.g. the abdomen, but it is preferred to place pump bulb 24 in the scrotum because the pump will be easier for the user to reach and operate. In pump bulb 24 is pump chamber 106. When pump bulb 24 is squeezed the fluid of said chamber is forced into tubing passageway 104 which is defined within tubing 26. At the anterior portion of pump bulb 24 is adapter 62 which function is to cap pump chamber 106 and serve as an adapter for tubing 26. Passageway 104 is in fluid communication with inflation chamber 96 of inflation block 42.

Figure 6:
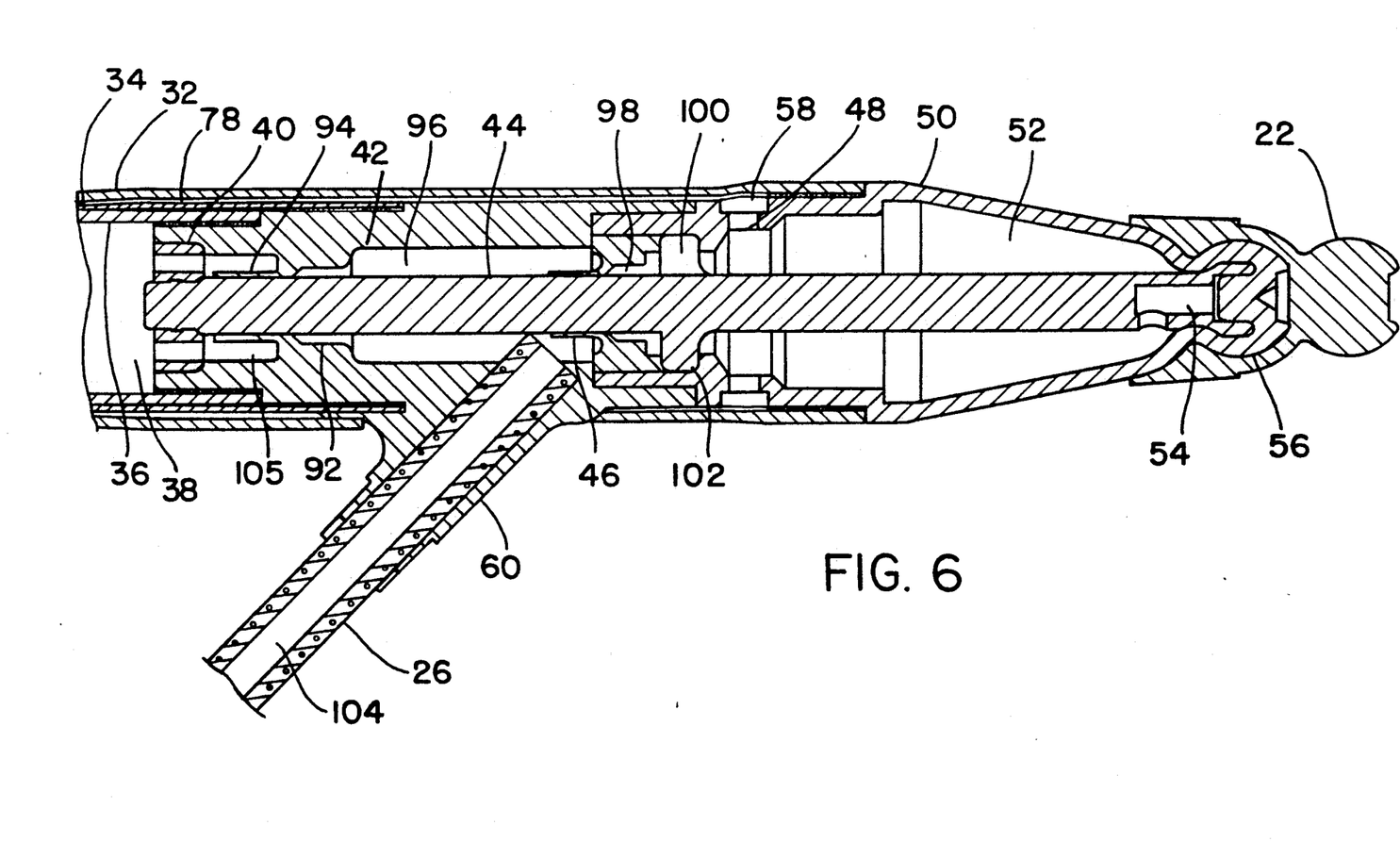
FIG. 6 is an enlarged cross-sectional view of the inflation valve assembly and reservoir shown in FIG. 2 with ingressing passageway from the pump bulb.

As shown in FIG. 6, inflation block 42 comprises an inflation chamber 96 which is circumferentially disposed about stiffener 44, the latter extending throughout most of the length of the proximal portion 14. Anteriorly placed in relation to such inflation chamber, as part of block 42, is a front check valve which comprises a skirt or thin-walled sleeve 94 which will open or close depending on the advent of pressure differential conditions, i.e. when the pressure of the inflation chamber 96 exceeds that of pressurizable chamber 38, the skirt 94 will open because positive pressure in chamber 96 will distend the sleeve (skirt) 94 and create a passageway between the inner walls of the skirt and stiffener 44. When the pressure of chamber 38 is greater than pressure in chamber 96 the valve will close, i.e. the positive pressure differential in pressurizable chamber 38 will compress the front skirt walls around the stiffener. In its normal mode, i.e. inactivated, skirt 94 is closed. Posteriorly placed in relation to said inflation chamber 96 is a rear check valve compressing a skirt or thin-walled sleeve 46 which is also adapted to open or close when subjected to pressure differential conditions. As with front check valve, the normal mode of the rear check valve is in a closed position. It is to be noted that "closed" means that the skirts are pressed against stiffener 44 thereby prohibiting the flow of fluid between the inner walls of said skirts and stiffener. The pressure differential conditions which will distend skirt 46 and open this valve, occur when the fluid pressure in reservoir 50 exceeds or is equal to that of inflation chamber 96. This valve will close when the fluid pressure of the inflation chamber exceeds or is equal to that of the reservoir.

Inflation chamber 96 is in fluid communication with pump chamber 106 through tubing passageway 104 at a point between front check valve formed by skirt 94, and rear check valve formed by rear skirt 46. Situated immediately rearwardly adjacent to rear skirt 46 are rear skirt passageways 98 which are in fluid communication with reservoir chamber 52 of reservoir 50 through passageways 100 located in stiffener flange 102. As stated, reservoir 50 is placed rearwardly in proximal portion 14. Stiffener flange 102 is disposed at a medial point in said proximal portion between rear skirt passageways 98 and inlet hole 48 to fix the stiffener 44 in the rear part of the cylinder. Snap washer 40 is disposed in front of skirt 94 to prevent inadvertent leakage of fluid from pressurizable chamber 38 into inflation chamber 96 through the front check valve when the chamber 38 is bent during intercourse or to effect deflation. The snap washer 40 defines a point beyond which the chamber 38 and adjacent front portion of inflation blank 42 cannot be bent.

Figure 5:
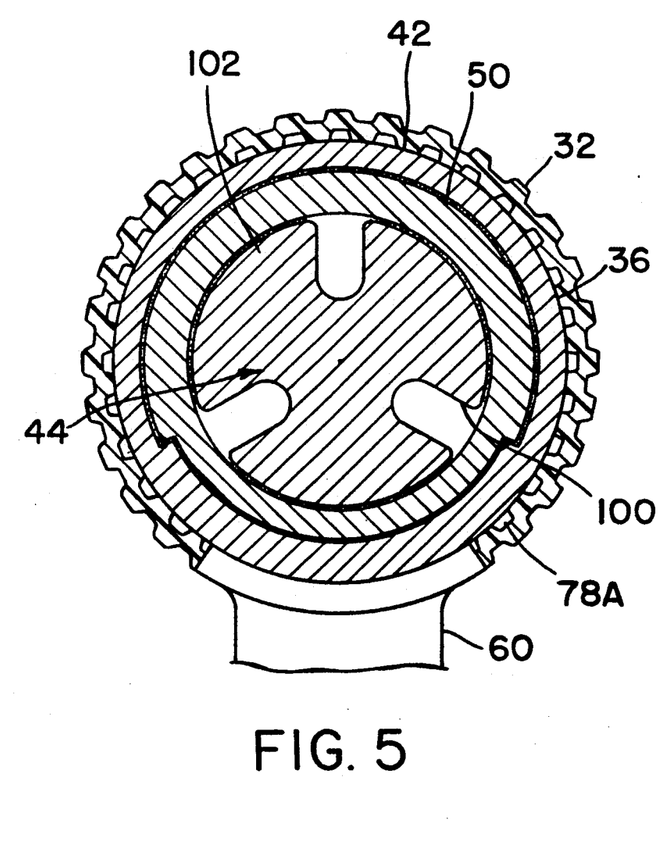
FIG. 5 is a transverse cross-sectional views along the axis 3—3 of the prosthesis of FIG. 2.

FIG. 5 is a transverse cross-sectional view of the rearward portion of inflation block 42 along the axis 3—3 of FIG. 2, which depicts in cross-sectional emphasis, the position of flange passageways 100 which enables fluid to pass from reservoir 50 into inflation chamber 96.

Figure 7:
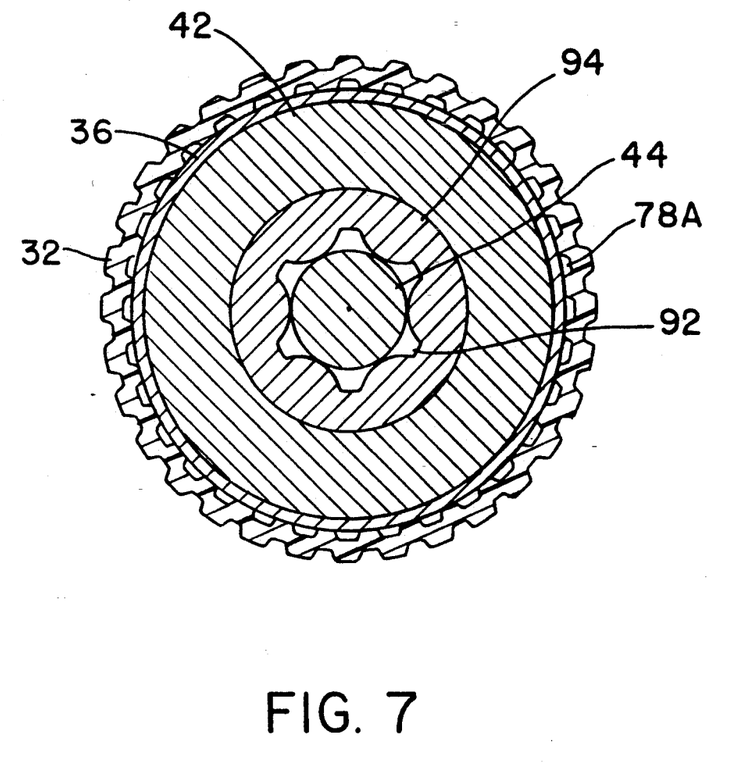
FIG. 7 is a transverse cross-sectional view along the axis 4—4 of the prosthesis of FIG. 2.

FIG. 7 is a further transverse cross-sectional view of inflation block 42 through the anterior position thereof, depicting the position in cross-sectional emphasis, of front skirt passageways 92 which permit the flow of fluid from inflation chamber 96 into pressurizable chamber 38. In both FIG. 5 and FIG. 7 passageways 78A are shown in transverse section.

Initially a sufficient amount of fluid is loaded into the device 10 in any suitable manner, such as for example through filling passageway 54 which is opened or closed employing reservoir plug 56. This procedure is described in U.S. Pat. No. 4,590,927. The prosthesis is implanted within the corpus cavernosum of the patient utilizing conventional surgical techniques well known in the implantation of penile prosthetic devices. Rear tip extenders can be employed to achieve a correct fit.

The preferred embodiment of this invention operates as follows:

To inflate the cylinders of this invention, after implantation, the user initially compresses the manually compressible pump bulb 24 which, as stated, is preferably located in the scrotum. The compression of the pump bulb 24 forces fluid contained in the pump chamber 106 into passageway 104 and then into inflation chamber 96 of inflation block 42. The passage of fluid into chamber 96 increases the pressure therein thereby creating a positive pressure differential between said chamber and anteriorly adjacent pressurizable chamber 38. As a consequence front skirt or sleeve 94 is forced opened permitting fluid to pass into pressurizable chamber 38. At the same time positive pressure differential between inflation chamber 96 and reservoir chamber 54 keeps rear skirt or sleeve 54 closed preventing fluid transmission from pump to reservoir. When pump bulb 24 is released, the vacuum or suction created in pump chamber 106 and inflation chamber 96 effects a positive pressure differential between reservoir 50 and inflation chamber 96. This then forces rear skirt or sleeve 46 to distend and open which thereby permits flow of fluid from reservoir 50 back into pump 24. Front skirt 94 at the same time closes because the pressure pressurizable chamber 38 is higher than in inflation chamber 96 which keeps front skirt 94 compressed around stiffener 44 and the front check valve closed. When the procedure is repeated, i.e. with the pump again being squeezed, the sequence is repeated with fluid again passing from the reservoir through the pump bulb into the inflation chamber and then into the pressurizable chamber. Repeated squeezing and releasing of the pump bulb, effectively will result in the passage of fluid into the chamber until full inflation, and erection, is accomplished.

It is noteworthy that in the practice of the device of this invention, the sequence of fluid flow is from pump to pressurizable chamber (through the inflation block chamber and front valve or skirt 94), then on releasing of the pump bulb, with consequent vacuum and suction, from reservoir to pump; and then again from pump to pressurizable chamber; until full inflation and erection occurs.

To resume the flaccid state after erection, part of the fluid from the pressurizable chamber 38 has to be transferred back to the reservoir 50. In accordance with this invention, this is done through the valve of deflation block 30 which in the practice of this invention is located in the distal (front) portion of device 10. Deflation valve 30 is normally in a closed mode due to the compression force of the spring 80 and, when pressurized, the pressure of the rear chamber 86. The fluid pressure in the rear chamber 86 and front chamber 64 of the deflation valve 30 is the same as in the pressurizable chamber 38, when the device 10 is in a flaccid or erect position.

To deflate the implanted prosthesis of this invention, after inflation, the user initially bends the penis somewhere along the pressurizable chamber 38, up or down, to or slightly more than a predetermined minimum angle which is typically established by the manufacturer of the prosthesis. For example, the angle can be set for operation at 50°-60° up or down from the original plane. However, the exact angle to be utilized is within the confines of practicality and user convenience. When the penis is bent to the deflation angle the fluid pressure in the pressurizable chamber 38 and in the rear chamber 86 of the deflation valve 30, which is in fluid communication with the chamber 38, in increased. The fluid pressure in the front chamber 64 of the deflation valve will also increase and will become equal to the increased fluid pressure of the rear chamber 86 and the pressurizable chamber 38. This will occur, however, after a short time delay caused by the fine-deferred passage of fluid from the front chamber to the rear chamber through the fluid resistor 88. The time delay (which can be predetermined) required to equalize pressure in chamber 38 and chamber 64, depends on the flow configuration of fluid resistor 88, the pressure differential between the front and rear chambers shortly after the penis is bent to the deflation angle, and the compliance of the front chamber 64, i.e. the ease with which the latter will expand under pressure. The increased pressure in the front chamber (while the same as that of the rear chamber) deflects the distensible partition or diaphragm 66 towards the poppet shaft 72. This deflection is directly proportional to the front chamber pressure and to the diameter of the diaphragm, and is inversely proportional to the thickness of the diaphragm.

However, at this point the sealing compression of the poppet head is still not affected because the pressures, though increased in both chambers, are still the same in all of those chambers.

After the predetermined time delay has expired, the user brings the penis back to the straight position abruptly. (Parenthetically, it must be stressed that the "time delays" referred to are measurement in seconds, e.g. on the order of 5 -10 seconds). When the penis is abruptly returned to the straight position, the fluid pressure in the pressurizable chamber 38 and the rear chamber 86 almost immediately returns to the initial level (i.e. to that level before the penis was bent to the deflation angle). However, the fluid pressure of the front chamber 64 will not return to the initial pressure as quickly i.e. it will remain higher for some time, (measured again in seconds) because the return flow of fluid from the front chamber 64 to the rear chamber 86 is again time-deferred because of the fluid resistor 88. Until this is done, there is thus a pressure differential between the front and rear chambers. Now the higher pressure of the front chamber causes the already deflected partition or diaphragm 66 to impact upon the poppet head 74 through poppet shaft 72. The latter is thereby pushed off its sealing contact with the valve seat 84 of the valve housing thus opening the deflation valve. The valve accordingly stays open until the pressure is equalized in the chamber 38 and in chamber 64. As previously described while the deflation valve 30 is open, fluid from the pressurizable chamber 38 flows to the reservoir 50 (because the latter has a lower pressure after the erect state has been induced). This is done through the communication conduit formed by the middle chamber 92, outlet hole 70, outlet ring channel 68, fluid passage channel 72, reservoir ring channel 58, inlet holes 48, into reservoir chamber 52.

However, while less desirable, it is also possible to operate the deflation valve of this invention, and accordingly to change the prosthetic of this invention from the erect to the flaccid state, without bending the penis to the deflation angle. Illustratively this could be done by directly increasing the pressure of the front chamber of the deflation valve by, for example, adding pressurized fluid from an outside source such as an implantable squeezable bulb filed with fluid which is connected by tubing or other suitable means directly to the front chamber. In this manner the pressure differential sequence, as defined above, could still occur within the valve. This might be advantageous to those users who have difficulty in bending or squeezing the penis.

It is also possible, although again less desirable, for the pressure conditions which will open the deflation valve to not require that the pressure of the front chamber of the valve be higher than that of the rear chamber. In this embodiment, the same, or essentially the same, pressure in the rear chamber can impact with sufficient force on the poppet to cause the valve to assume an open mode, if the area of the wall of the movable or distensible partition is sufficiently larger than the area of the poppet head. The same time deferred sequence will then still serve to shift the pressures from the rear to front chamber. However, because the force exerted will be proportional to the area of the partition as well as the pressure of the rear chamber, the latter pressure need not be greater than that of the rear chamber to cause the distensible or movable partition to impact upon the poppet with sufficient force to cause the latter to break sealing contact with the valve housing.

It is also apparent that modification and variations besides those specifically mentioned herein may be made in the structures and techniques described herein and depicted in the accompanying drawings without departing from the concept of the present invention.

We claim:

1. A penile prosthesis having a generally tubular enclosure having a proximal portion and a distal portion implantable within a corpus cavernosum of the penis, said tubular enclosure comprising:
   a generally tubular non-distensible pressurizable chamber having an interior volume defined substantially medially within said enclosure, said prosthesis being transformable from a flaccid to an erect state when the interior volume of said pressurizable chamber is filled with fluid substantially to capacity;
   a fluid containing reservoir defined within the proximal portion of said enclosure;
   an inflation assembly comprising two valves in longitudinally sequential relationship, said valves having means for opening and closing under sequentially applied pressure differential conditions, said assembly being disposed between the pressurizable chamber and the reservoir;
   and a deflation valve defined within the distal portion of said enclosure, adjacent to the pressurizable chamber;
   said prosthesis also including a pump bulb which is adapted to be implanted separate from said enclosure and in a part of the body apart from the penis, said pump bulb being in fluid communication with said inflation assembly through a passageway exiting into said inflation assembly at a location between said two inflation valves of said inflation assembly;
   whereby to inflate the prosthesis the pump bulb is sequentially squeezed and released so that fluid will flow from the pump bulb to the pressurizable chamber, from the reservoir back to the pump bulb, and back again to the pressurizable chamber until the latter is filled to capacity causing the prosthesis to assume the erect state.

2. A penile prosthesis having a generally tubular enclosure having a proximal portion and a distal portion implantable within a corpus cavernosum of the penis, said tubular enclosure comprising:
   a generally tubular non-distensible pressurizable chamber having an interior volume defined substantially medially within said enclosure, said chamber being transformable from a flaccid to an erect state when the interior volume of said chamber is filled with fluid substantially to capacity;
   a fluid containing reservoir defined within the proximal portion of said enclosure;
   an inflation assembly disposed between the pressurizable chamber and the reservoir and comprising two valves in longitudinally sequential relationship, said valves having means for opening and closing under sequentially applied pressure differential conditions, said means for each valve comprising a normally tightly fitting but distensible sleeve which in a closed mode will be compressed on a rigid portion of the inflation assembly, but in an open mode will enable fluid to pass around said portion from an adjacent chamber;
   and a deflation valve defined within the distal portion of said enclosure, adjacent to the pressurizable chamber;
   said prosthesis also including a pump bulb for implantation separate from the tubular enclosure, said pump bulb being in fluid communication with said inflation assembly through a passageway exiting into said inflation assembly at a location between said two inflation valves of said inflation assembly;
   whereby when said pump bulb is sequentially squeezed and released fluid will flow from the pump bulb to the pressurizable chamber, from the reservoir back to the pump bulb, and back again to the pressurizable chamber until the latter is filled to capacity causing the prosthesis to assume the erect state.

3. A penile prosthesis in accordance with claim 1, wherein the pump bulb is adapted to be implanted within the scrotum.

4. A penile prosthesis in accordance with claim 3, wherein the tubular enclosure comprises a proximal portion, a distal portion, and a medial portion, having an outer layer wherein the outer layer of said medial portion has a corrugated configuration.

5. A penile prosthesis in accordance with claim 4, wherein the corrugated configuration of the outer layer of the medial portion defines a series of passageways or channels permitting the flow fluid from the deflation valve to the reservoir.

6. A penile prosthesis in accordance with claim 4, wherein the distal portion is substantially rigid.

7. A penile prosthesis in accordance with claim 4, wherein the pressurizable chamber includes a substantially non-distensible tubular portion, and a tubular sleeve concentric with said tubular portion, and wherein said tubular sleeve contains channels which permit the flow of fluid during deflation from the pressurizable chamber back to the reservoir.

8. A penile prosthesis having a generally tubular enclosure having a proximal portion and a distal portion implantable within a corpus cavernosum of the penis, said tubular enclosure comprising:
   a generally tubular non-distensible pressurizable chamber having an interior volume defined substantially medially within said enclosure, said chamber being transferable from a flaccid to an erect state when the interior volume of said chamber is filled with fluid substantially to capacity;
   a fluid containing reservoir defined within the proximal portion of said enclosure;
   an inflation assembly between the pressurizable chamber and the reservoir comprising two valves in longitudinally sequential relationship adapted to open and close under sequentially applied pressure differential conditions, said assembly also including an inflation chamber circumferentially disposed about a stiffener, the stiffener extending throughout most of said proximal portion, the valves comprising a front check valve consisting of a sleeve normally tightly affixed to the stiffener which will distend and thereby open when the pressure of the inflation chamber exceeds that of the pressurizable chamber and will close when the pressure of the pressurizable chamber exceeds that of the inflation chamber, and a rear check valve which consists of a sleeve normally tightly affixed to the stiffener which will distend and thereby open when the fluid pressure in the reservoir exceeds that of the inflation chamber and will close when the pressure of the inflation chamber exceeds or is equal to that of the reservoir;

and a deflation valve defined within the distal portion of said enclosure, adjacent to the pressurizable chamber;

said prosthesis also including a pump bulb for implantation separate from the tubular enclosure, said pump bulb being in fluid communication with said inflation assembly through a passageway exiting into said inflation assembly at a location between said two inflation valves of said inflation assembly;

whereby when said pump bulb is sequentially squeezed and released fluid will flow from the pump bulb to the pressurizable chamber, from the reservoir back to the pump bulb, and back again to the pressurizable chamber until the latter is filled to capacity causing the prosthesis to assume the erect state.

9. A penile prosthesis having a generally tubular enclosure having a proximal portion and a distal portion implantable within a corpus cavernosum of the penis, said tubular enclosure comprising:

a generally tubular non-distensible pressurizable chamber having an interior volume defined substantially medially within said enclosure, said chamber being transferable from a flaccid to an erect state when the interior volume of said chamber is filled with fluid substantially to capacity;

a fluid containing reservoir defined within the proximal portion of said enclosure;

an inflation assembly between the pressurizable chamber and the reservoir comprising two valves in longitudinally sequential relationship adapted to open and close under sequentially applied pressure differential conditions, said assembly also including an inflation chamber circumferentially disposed about a stiffener, the stiffener extending throughout most of said proximal portion, the valves comprising a front check valve consisting of a sleeve normally tightly affixed to the stiffener which will distend and thereby open when the pressure of the inflation chamber exceeds that of the pressurizable chamber and will close when the pressure of the pressurizable chamber exceeds that of the inflation chamber, and a rear check valve which consists of a sleeve normally tightly affixed to the stiffener which will distend and thereby open when the fluid pressure in the reservoir exceeds that of the inflation chamber and will close when the pressure of the inflation chamber exceeds or is equal to that of the reservoir;

and a deflation valve for returning said pressurizable chamber from the erect to flaccid state, said valve being in fluid communication with said pressurizable chamber and said reservoir, said valve comprising closure means for normally keeping the valve in a closed mode, means for time-deferring the transfer of fluid within said valve thereby effecting a change in the internal pressure conditions within said valve, and a movable partition disposed within a distensible chamber within said valve capable of exerting sufficient force upon said closure means as a consequence of said change in internal pressure conditions, to place said valve in an open mode necessary to cause deflation;

said prosthesis also including a pump bulb for implantation separate from the tubular enclosure, said pump bulb being in fluid communication with said inflation assembly through a passageway exiting into said inflation assembly at a location between said two inflation valves of said inflation assembly;

whereby when said pump bulb is sequentially squeezed and released fluid will flow from the pump bulb to the pressurizable chamber, from the reservoir back to the pump bulb, and back again to the pressurizable chamber until the latter is filled to capacity causing the prosthesis to assume the erect state.

10. A penile prosthesis in accordance with claim 9, wherein said deflation valve for returning said chamber section from the erect to flaccid state comprises a housing having defined therewithin:

closure means comprising a poppet having a head and shaft, and including means for exerting a force upon said poppet head for normally keeping the sealing edge thereof in sealing contact with the inner surface of said housing;

said poppet head being disposed within a chamber containing fluid, said chamber being in fluid communication with said pressurizable chamber, the fluid pressure in said chamber and said means for exerting a force upon said poppet head normally keeping the closure means and thereby the valve mechanism in a closed mode;

a movable partition capable of impacting upon said poppet;

and a further distensible chamber adjacent to said partition, said chamber being in fluid communication with the chamber disposed about the poppet head through means which time-defer the transfer of fluid between said chambers; whereby under precalibrated pressure conditions fluid pressure in said further chamber will distend said partition to exert sufficient force upon said poppet to break the sealing contact of said poppet head with said housing, thereby placing the valve mechanism in an open mode, whereby fluid from said tubular pressurizable chamber will flow into the chamber disposed about the poppet head and then into said fluid reservoir thereby deflating said tubular chamber section and returning said section to its flaccid state.

11. A penile prosthesis in accordance with claim 10, wherein to effect said precalibrated pressure differential conditions within the deflation valve the pressurizable chamber section is initially bent to a predetermined extent so that the fluid pressure in the chamber disposed about the poppet head is sharply increased, and is then quickly returned to its unbent position so that the fluid pressure in the chamber disposed about the poppet head is sharply decreased back to its original pressure, but wherein because of the time-delay occasioned by the means which transfers the flow of fluids to and from said latter chamber to the chamber disposed adjacent to the distensible partition, the pressure of the latter chamber is differentially higher than that of the chamber disposed about the poppet head, said higher pressure thereby distending the partition and causing it to impact upon the poppet thereby opening said deflation valve.

12. A penile prosthesis in accordance with claim 11, wherein the means which time-defer the transfer of fluid between the chamber disposed about the poppet head and the further chamber disposed adjacent to the distensible partition comprises fluid resistor means, and the distensible partition is a distensible diaphragm.

13. A penile prosthesis in accordance with claim 12, wherein the pump bulb is adapted to be implanted within the scrotum.

* * * * *